United States Patent [19]

Claremon et al.

[11] Patent Number: 5,084,444
[45] Date of Patent: Jan. 28, 1992

[54] IMIDAZOLE COMPOUNDS AND THEIR USE AS TRANSGLUTAMINASE INHIBITORS

[75] Inventors: David A. Claremon, Audubon; John J. Baldwin, Gwyneed Valley; David C. Remy, North Wales, all of Pa.

[73] Assignee: Merck & Co. Inc., Rahway, N.J.

[21] Appl. No.: 712,781

[22] Filed: Jun. 10, 1991

Related U.S. Application Data

[62] Division of Ser. No. 386,644, Jul. 31, 1991.

[51] Int. Cl.⁵ .......................... A61K 37/02; C07K 7/06
[52] U.S. Cl. .......................................... 514/15; 514/16; 514/18; 514/393; 530/328; 530/329; 530/331
[58] Field of Search ................ 530/328, 329; 514/15, 514/16, 18, 393

[56] References Cited

U.S. PATENT DOCUMENTS 4,172,139 10/1979 Eakins et al. ................. 514/400
4,487,718 12/1984 Aoki et al. ..................... 530/327
4,868,197 9/1989 Schnettler et al. ............. 548/321

OTHER PUBLICATIONS

Kister et al., Can J. Chem 57,813 (1979).
Kister et al., Can J. Chem 57,822 (1979).

*Primary Examiner*—Lester L. Lee
*Assistant Examiner*—S. G. Marshall
*Attorney, Agent, or Firm*—Alice O. Robertson; Hesna J. Pfeiffer

[57] ABSTRACT

Imidazole compounds including imidazoles and imidazolium salts, and their use as transglutaminase inhibitors are disclosed.

7 Claims, No Drawings

IMIDAZOLE COMPOUNDS AND THEIR USE AS TRANSGLUTAMINASE INHIBITORS

This is a division of application Ser. No. 07/386,644, filed July 31, 1991.

BACKGROUND OF THE INVENTION

Transglutaminase, also known as transamidases, are a family of enzymes which catalyze the amide bond formation of the γ-carboxamide group of peptide glutamine residues with an ε-amino group of peptide lysine residues.

A number of disease states have been associated with transglutaminase activity. Thus, for example, in acne lesions, transglutaminase activity in sebaceous follicles has been reported by DeYoung et. al., in J. Investigative Dermatology, 82, 275 (1984). Also, the cornified cell envelope in acne has been reported to be a result of transglutaminase activity by Dalziel et. al., Br. J. Exp. Pathology, 65, 107-115 (1984).

Another dermatological disease, psoriasis, is reported to be associated with excessive transglutaminase activity by Bernard et. al. British Journal of Dermatology, 114, 279 (1986).

Cataracts also have been reported to be associated with elevated transglutaminase activities.

Factor XIIIa is a plasma transglutaminase which is the activated form of Factor XIII also known as fibrinase or fibrin-stabilizing factor. It is essential for normal hemostatis and is responsible for the cross-linking of fibrin.

While the activity of this enzyme may be desirable and essential under most circumstances, activity under certain other circumstances can be highly undesirable. Thus, excessive thrombosis, that is, the formation of clot within a blood vessel, gives rise to thrombotic strokes, deep vein thrombosis, variant angina, myocardial infarction, and other medical conditions which frequently result in necrosis of tissues and oftentimes in death of a patient. Even if death does not occur, thrombotic attacks are accompanied by damage to cells to which circulation has been prevented by thrombi formation. Removal of the thrombi by lysis is essential and the rate of lysis may be critical in ultimate patient recovery.

Lysis may occur normally in hours or days by the action of a proteolytic enzyme, plasmin, which is present in plasma as the inactive precursor, plasminogen, and which is activated by plasminogen activators, such as (pro)urokinase, urokinase or tissue plasminogen activator (tPA). Since the occurrence of a thrombotic event calls for rapid remedial action, administration of exogenous tissue plasminogen activator or (pro)urokinase is currently looked to in thrombolytic or fibrinolytic therapy. However, a still further reduction in lysis time is necessary to minimize cell injury.

Since Factor XIIIa is an enzyme responsible for the final event in the coagulation of blood, lysis and maintaining the lytic state can be facilitated by the presence of a Factor XIIIa inhibitor. Moverover, the presence of a Factor XIIIa inhibitor as in a prophylactic treatment would inhibit hard clot formation where thrombosis can be anticipated. Thus, a Factor XIIIa inhibitor is useful in inhibiting thrombosis, in treating thrombosis when used with a plasminogen activator, a platelet aggregation inhibitor, or anticoagulant and in post fibrinolytic therapy in maintaining the lytic state.

STATEMENT OF THE INVENTION

A novel class of imidazole compounds has been discovered which inhibits transglutaminase activity, particularly Factor XIIIa activity. The invention also embraces composition and methods for using the imidazole compounds as Factor XIIIa inhibitors in fibrinolytic or thrombolytic therapy. For use as Factor XIIIa inhibitors, the compounds may be used alone or together with agents used in thrombolytic or fibrinolytic therapy such as a plasminogen activator, a platelet aggregation inhibitor or an anticoagulant.

DETAILED DESCRIPTION OF THE INVENTION

The imidazole compounds of the present invention is a compound selected from the group consisting of:

(A) an imidazole represented by the formula

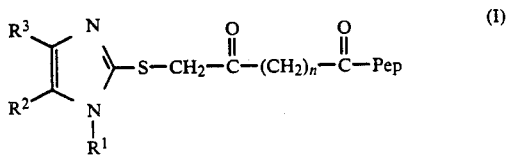

(I)

or its acid addition salt, and (B) an imidazolium salt represented by the formula

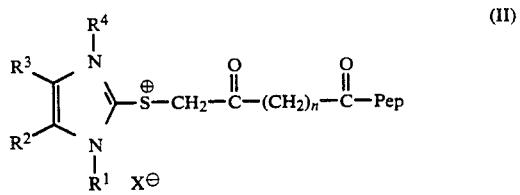

(II)

In the foregoing and succeeding formulas, $R^1$ is lower alkyl, $R^2$ and $R^3$ are independently hydrogen or lower alkyl, or $R^2$ and $R^3$ taken together is an alkylene chain of from 3 to 10 carbon atoms, $R^4$ is lower alkyl and Pep is a peptidyl chain of 2 to 10 amino acids which is attached to the carbonyl through the α-amino of the amino acid and which terminates with the carbonyl group of the amino acid in an amide linkage with the $NH_2$ originating from a source outside the amino acid; and X is a negative radical of a pharmaceutically acceptable salt; and n is from 2 to 5.

The specific peptidyl chain which is generically embraced by "Pep" may be identified by naming the amino acid sequence, employing conventional abbreviation used for the amino acid. Representative of but not inclusive are the following abbreviations which are most frequently used in the present application: Glu=glutamic acid; Gln=glutamine; Val=valine; Ser=serine; Pro=proline; Leu=leucine; Thr=threonine; Gly=glycine; Lys=lysine. Since the peptide chain is a synthetic one, both natural and unnatural amino acids are contemplated and not limited to the foregoing.

Pharmaceutically acceptable salts suitable as acid addition salts as well as providing the anion of the imidazolium salts are those from acids such as hydrochloric, hydrobromic, hydroiodic, phosphoric, sulfuric, trifluoroacetic, trichloroacetic, oxalic, maleic, pyruvic, malonic, succinic, citric, mandelic, benzoic, cinnamic, methanesulfonic, ethanesulfonic, trifluoromethanesulfonic and the like, and include other acids related to the pharmaceutically acceptable salts listed in Journal of Pharmaceutical Science, 66, 2 (1977) and incorporated herein by reference.

By the expression "lower alkyl" as employed in the specification and claims is meant radicals having from 1 to 6 carbon atoms.

The compounds, both those which are acid addition salts of the compounds represented by formula (I) and those quaternary salts represented by formula (II) are soluble in polar solvents such as water, methanol, ethanol, dimethyl sulfoxide, dimethylformamide and the like. The imidazoles of formula (I) are soluble in non-polar solvents such as ethyl acetate, methylene chloride, diethylene chloride, carbon tetrachloride and the like.

The compounds of the present invention are useful as transglutaminase inhibitors, particularly as Factor XIIIa inhibitors, and are adapted to be employed in thrombolytic therapy. In such use, it is administered to a thrombotic patient for more rapid lysis of blood clots or to patients susceptible to thrombotic attack either alone or in combination. Preferably, it is employed together with a plasminogen activator, an enzyme which converts plasminogen to plasmin to increase the rate and extent of lysis. Suitable activators include tissue plasminogen activator (tPA), prourokinase (single chain urokinase), urokinase (dual chain urokinase), streptokinase and eminase (European patent application 028,489). The plasminogen activators may be those isolated from natural sources or produced by recombinant technology and include the genetically engineered variants thereof.

Also, it may be employed together with platelet aggregation inhibitors. Platelet aggregation inhibitors may be drugs, naturally occurring proteins or peptides or may be modified or semi-synthetic proteins or peptides.

Established drugs which are platelet aggregation inhibitors include aspirin and dipyridamole. Proteins or polypeptides which are platelet aggregation inhibitors have a certain peptide sequence, most frequently Arg-Gly-Asp. Some classes of natural proteins having this property are fibrinogen receptor antagonists, thromboxane receptor antagonists, thromboxane synthesis inhibitors, collagen receptor antagonists and thrombin inhibitors. Among especially useful polypeptides are those designated "Echistatin" and "Bitistatin" and having the amino acid sequence: X-Cys-R-R-R-Arg-Gly-Asp-R-R-R-R-R-Cys-Y where X is H or an amino acid, Y is OH or an amino acid and each R independently is amino acid, described and claimed in copending applications Ser. No. 184,649, filed Apr. 22, 1988; Ser. No. 303,757, filed Feb. 1, 1989; and Ser. No. 307,642 filed Feb. 7, 1989, all in the names of P. A. Friedman, et al., the teachings of which are incorporated by reference.

Additionally, the imidazole compounds may be employed for continued therapy after initial relief from thrombotic attack providing a more complete lysis thereby minimizing complications from reocclusion. Moreover, the imidazole compounds may be employed in post thrombosis therapy together with anticoagulants such as heparin and coumarin drugs.

The preferred compounds for use as transglutaminase inhibitors are the quaternary imidazolium salts.

The compounds to be employed in the practice of the present invention which are imidazoles may be intermediates in the preparation of those compounds which are imidazolium salts. However, the latter compounds may be prepared by an alternate procedure in which an imidazole is not an intermediate.

The imidazoles (I) useful in the present invention may be prepared according to the following flow diagram:

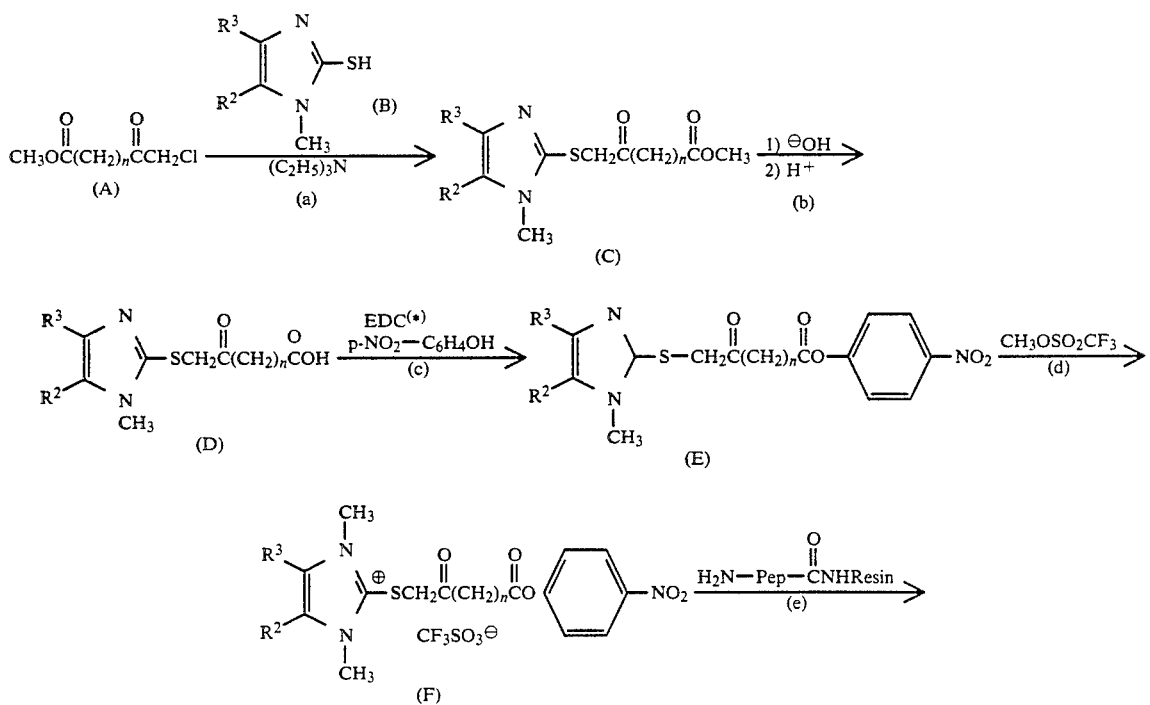

-continued

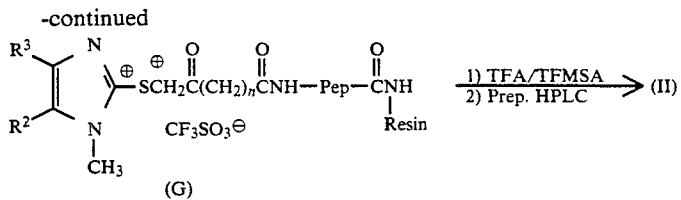

(G)

(*)or pentachlorophenol

The sequence of the flow diagram may be modified so that the condensation of the peptide chain to compound (D) may be caused to occur to obtain imidazole (I).

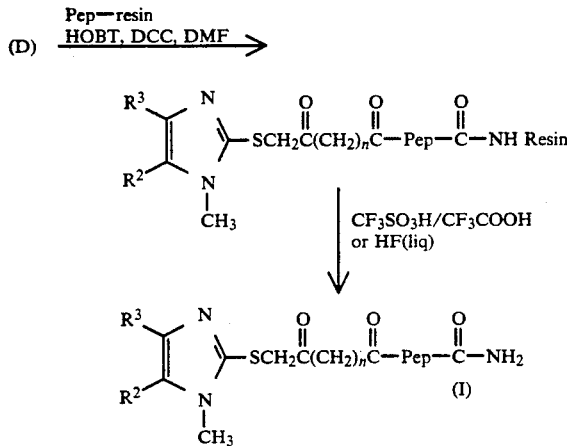

In Step (a) the appropriate acylmethyl chloride (A) is caused to react with an appropriate 2-mercaptoimidazole (B) to produce the acylmethylthioimidazole ester compound (C). In carrying out the reaction, a solution of the acylmethyl chloride is added dropwise to a cooled suspension of the mercaptoimidazole and a tertiary amine. Triethylamine is a preferred amine although other common tertiary amines may be employed. Suitable solvents for both reactants include acetone, methyl ethyl ketone, methylene chloride and the like. After completion of the addition the resulting mixture is stirred for from several hours to overnight to complete the reaction with the formation of the imidazole compound (C). The latter is recovered from the reaction mixture by conventional processes of (i) concentrating, (ii) dissolving in water-immiscible organic solvent such as ethyl acetate, (iii) washing, (iv) drying and concentrating the dried solution.

Next, in Step (b) the ester compound (C) is hydrolyzed to the acid compound (D). The hydrolysis may be carried out by intimately contacting the ester compound with an aqueous alkali metal hydroxide solution. A molar excess of the base is employed. Generally, 10 to 25 percent molar excess is satisfactory. Suitable alkali metal hydroxides are lithium hydroxide, potassium hydroxide and sodium hydroxide. The reaction may be carried out in a water miscible solvent such as tetrahydrofuran, ethanol, and the like, at ambient temperature for from a few hours to overnight. When the reaction is complete, the reaction mixture is first concentrated, the concentrate then is dissolved in water, and the aqueous solution extracted with a water-immiscible solvent such as ethyl acetate to remove unreacted material and water-insoluble impurities. Thereafter, the aqueous solution is acidified to pH about 6.0 and the acidified aqueous solution continuously extracted for from several hours to several days with ethyl acetate to obtain the desired acid (D).

Then, in Step (c), the acid is converted to an aromatic ester which is a reactive ester suitable for the next step. Although various aromatic hydroxy compounds may be employed, the preferred aromatic hydroxy compound is p-nitrophenol and the reaction is illustrated with p-nitrophenol to obtain the nitrophenyl ester. Other representative hydroxy compounds are pentachlorophenol and pentafluorophenol. The ester may be prepared by reacting the acid (D) with nitrophenol in the presence of a dehydrative coupling agent. A suitable coupling agent is 1-(3-dimethylaminopropyl)-3-ethylcarbodiimide hydrochloride (EDC). A slight molar excess of the nitrophenol and the coupling agent are employed. The reaction is carried out in an inert solvent for several hours or overnight. Suitable solvents include methylene chloride and dimethylformamide. After the reaction is complete, the reaction mixture is diluted with ethyl acetate and compound (E) recovered therefrom by conventional procedures such as washing, drying and concentrating.

Then, in Step (d) Compound (E) is converted to the imidazolium salt by intimately contacting the compound with methyl trifluoromethanesulfonate to obtain 1,3-dimethyl-2-[p-ω(p-nitrophenoxy)-2,ω-dioxoalkylthio]-imidazolium trifluoromethanesulfonate (F).

The above two steps may be carried out without the initial isolation of the reactive ester (E). In such case the trifluoromethanesulfonate is added to the reaction mixture in which the ester was formed.

Next, in Step (e) the imidazolium salt (Compound F) is then caused to react with a previously prepared peptide bearing solid phase resin.

The peptide chain is prepared by the solid phase method of R. B. Merrifield described in a chapter by G. Barany and R. B. Merrifield in "The Peptides" Vol. 2, p. 14–84 Academic Press, Inc. Orlando, Fla., 1979. The process entails sequentially coupling an amino acid on a methylbenzohydrylamine resin. In the method, a protected amino acid is coupled through the carboxyl group to the amino group on the resin; then the protecting group is removed and the next protected amino acid is coupled to first amino acid and the procedure repeated until the desired chain is obtained. At this time, the peptide chain still bearing the resin is ready for reaction with the active ester (F).

The active ester either before or after conversion to the imidazolium salt (Compound E or F) is intimately mixed with the peptide chain on the resin in an inert solvent such as dimethylformamide, methylene chloride and the like. The mixture is stirred until the Kaiser test is negative. (The Kaiser test is a color test for the detection of free terminal amino groups in the solid phase synthesis of peptides. Analytical Biochemistry, 34, 595 (1970)). The peptide resin is then washed and recovered. The resin is then removed from the peptide by intimately contacting the peptide-resin with trifluoroacetic acid and anhydrous trifluoromethanesulfonic acid or with anhydrous hydrofluoric acid whereupon the peptide bearing imidazole compound (I or II) is obtained. In the cleavage with the foregoing reagents, the amino group originally on the resin is cleaved with the peptide so that the terminal amino acid separates as an amide. The compound may be recovered according to conventional methods.

The usefulness of the compounds as Factor XIIIa inhibitors for enchancing the rate of clot lysis catalyzed by plasminogen activators may be demonstrated first by establishing the inhibitory potencies of the compounds in a Factor XIIIa assay.

The Factor XIIIa inhibitor assay is based on the incorporation of $^{14}$C-putrescine into casein catalyzed by Factor XIIIa. The assay is carried out employing the procedure described in Methods in Enzymology, Vol. 45, Ch 15., pages 177-191 (1976) and using Factor XIII (F XIII) isolated from human plasma. The procedure is summarized briefly and schematically illustrated as follows:

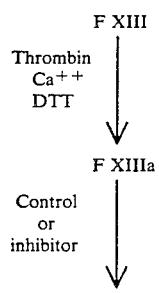

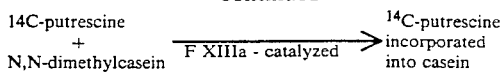

Factor XIII assay mixtures are prepared by adding stepwise, appropriately prepared solutions of thrombin and dithiothreitol (DTT) to a mixture comprising Factor XIII at 140 µg/mL in glycerol/water and tris(hydroxymethyl)aminomethane hydrochloride (Tris.HCl). To a portion of the mixture is added calcium chloride as source of calcium ions required for enzyme activity and to the remaining mixture is added, instead of calcium ions, ethylenediaminetetraacetic acid (EDTA) which serves as a blank for background.

A substrate mixture is prepared from $^{14}$C-putrescine and N,N-dimethylcasein.

The assay tubes and control tubes are charged with the substrate mixture and incubated at 37° C. for 20 minutes. Samples are withdrawn from each tube, spotted onto a filter disk which is then immersed in ice cold trichloroacetic acid solution to precipitate the casein on the filter. The filter is then washed to remove unincorporated or free $^{14}$C-putrescine and after drying is counted for $^{14}$C-putrescine incorporated to casein from which percent activity and/or inhibition can be calculated.

Imidazole compounds showing at least 50 percent activity at $2 \times 10^{-5}$M in the Factor XIIIa assay are considered to be useful in inhibiting hard clot formation or especially in supplementing fibrinolysis by plasminogen activator.

The imidazoles and imidazolium salts seen in Table I are representatives of compounds having IC$_{50}$ at concentrations below $2 \times 10^{-5}$M. Also seen in Table I are the properties of the various compounds.

TABLE I

| Com# No. | R$^1$ | R$^2$ | R$^3$ | R$^4$ | Pep | n | Salt or Anion | Mass Spectra |
|---|---|---|---|---|---|---|---|---|
| 1 | CH$_3$ | H | H | CH$_3$ | Glu—Gln—Val—NH$_2$ | 3 | Cl$^-$ | 613 |
| 2 | CH$_3$ | H | H | CH$_3$ | Glu—Gln—Val—Ser—Pro—Leu—Thr—NH$_2$ | 3 | Cl$^-$ | 1011 |
| 3 | CH$_3$ | H | H | CH$_3$ | —R—Lys—NH$_2$<br>    |<br>(CH$_2$)$_4$NH$_3$ | 3 | 2TFA$^-$ | 1309 |
| 4 | CH$_3$ | H | H | CH$_3$ | —R—Lys—NH$_2$ ⊕<br>    |<br>(CH$_2$)$_4$NHCOCH$_2$C$_6$H$_4$Cl(o) | 3 | Cl$^-$ | 1479 |
| 5 | CH$_3$ | H | H | H | Glu—Gln—Val—NH$_2$ | 3 | — | 598.4 |
| 6 | CH$_3$ | H | H | H | Glu—Glu—Val—Ser—Pro—Leu—Thr—NH$_2$ | 3 | — | 996 |
| 7 | CH$_3$ | H | H | H | —R—Lys—NH$_2$ | 3 | — | 1294 |
| 8 | CH$_3$ | H | H | H | —R—Lys—NH$_2$ | 4 | — | 1308.2 |
| 9 | CH$_3$ | H | H | H | —R—Lys—NH$_2$ .TFA<br>    |<br>(CH$_2$)$_4$NHCOOCH$_2$C$_6$H$_4$Cl(o) | 4 | — | 1476.2 |
| 10 | CH$_3$ | H | H | H | —R—Lys—NH$_2$ 2TFA | 2 | 2CF$_3$COO$^-$ | 1280.7 |
| 11 | CH$_3$ | H | H | CH$_3$ | —R—Lys—NH$_2$ | 2 | CF$_3$COO$^-$ | 1294.7 |
| 12 | CH$_3$ | H | H | CH$_3$ | —R—Lys—NH$_2$ | 4 | CF$_3$COO$^-$ | 1322.3 |
| 13 | CH$_3$ | H | H | CH$_3$ | —R—Lys—NH$_2$<br>    |<br>(CH$_2$)$_4$—NH(COOCH$_2$C$_6$H$_4$Cl(o) | 4 | CF$_3$COO$^-$ | 1490.2 |
| 14 | CH$_3$ | CH$_3$ | CH$_3$ | — | —R—Lys—NH$_2$ | 3 | ″ | 1322.4 |

TABLE I-continued

| Com# No. | $R^1$ | $R^2$ | $R^3$ | $R^4$ | Pep | n | Salt or Anion | Mass Spectra |
|---|---|---|---|---|---|---|---|---|
| 15 | $CH_3$ | $CH_3$ | $CH_3$ | — | —R—Lys—$NH_2$<br>\|<br>$(CH_2)_4$<br>\|<br>$NHCOOCH_2C_6H_4Cl_{(o)}$ | 3 | " | 1492.2 |
| 16 | $CH_3$ | $CH_3$ | $CH_3$ | $CH_3$ | —R—Lys—$NH_2$ | 3 | $CF_3COO^-$ | 1337.8 |
| 17 | $CH_3$ | $CH_3$ | $CH_3$ | $CH_3$ | —R—Lys—$NH_2$<br>\|<br>$(CH_2)_4$<br>\|<br>$NHCOOCH_2C_6H_4Cl_{(o)}$ | 3 | $CF_3COO^-$ | 1504.6 |
| 18 | $CH_3$ | $CH_3$ | $CH_3$ | $CH_3$ | —R—Lys—$NH_2$ | 5 | $CF_3COO^-$ | 1323.9 |
| 19 | $CH_3$ | $CH_3$ | $CH_3$ |  | —R—Lys—$NH_2$ | 5 | " | 1308.7 |
| 20 | $CH_3$ | $CH_3$ | $CH_3$ | — | —R—$NH_2$ | 4 | " | 1336 |
| 21 | $CH_3$ | $CH_3$ | $CH_3$ | $CH_3$ | —R—$NH_2$ | 4 | $CF_3COO^-$ | 1351.4 |

R = Glu—Gln—Val—Ser—Pro—Leu—Thr—Gly—Leu

For use in facilitating or supplementing fibrinolytic therapy, the imidazole compound may be administered in a pre- or post-lytic state alone or in combination therapy. Preferably, it is used in a combination therapy with a plasminogen activator, with a platelet aggregation inhibitor or with natural and synthetic anticoagulants.

The process for facilitating or supplementing fibrinolytic therapy in prothrombic patients comprises administering a therapeutic dose of an imidazole compound in an amount to provide between 1.4–140 mg/kg/day while considering patient's health, weight, age and other factors which influence drug response. The drug may be administered per os or by injection, and if by injection, either by single injection, multiple injections or continuous infusion.

In the preferred process of the present invention, the imidazole compound is administered with a plasminogen activator in a combination therapy. When combination therapy is employed, it is preferable to administer the Factor XIIIa inhibitor imidazole compound first in a single bolus and thereafter to administer the plasminogen activator by continuous infusion. However, both may be administered simultaneously as a continuous infusate. Under certain circumstances it may be desirable to administer the imidazole compound subsequent to the administration of the plasminogen activator. It is intended that the method of the present invention embrace concurrent administration as well as sequential administration, in any order.

When the Factor XIIIa inhibitor imidazole compound and plasminogen activator are employed in a combination therapy, it is most desirable to use the plasminogen activator in the dose range of about 500 to 10,000 I.U./kg/minute for from about 30 to 180 minutes and the imidazole compound in the range of 1 μg–100 μg/kg/minute for a day (1440 minutes).

When the imidazole compound is to be used with a platelet aggregation inhibitor in combination therapy, the dose range for platelet aggregation inhibitor depends on the nature of the inhibitor. When the platelet aggregation inhibitor is aspirin, the aspirin may be employed at a dose of 25–325 mg twice a day. When the platelet aggregation inhibitor compound is dipyridamole, the dipyridamole may be employed at a dose of 25–100 mg four times a day. When the platelet aggregation inhibitor is a semi-synthetic peptide such as "Echistatin" or "Bitistatin", the peptide may be administered in a dose range of 0.1 to 1 nanomole/kg/min. for from 30 to 180 minutes. In each case, the imidazole compound may be employed in the range of 1-100 μg/kg/min. for a day. The administration may be carried out simultaneously or sequentially in any order as in the procedure for administration with plasminogen activators.

When the imidazole compound is to be used with heparin, heparin may be administered at doses of 4000 to 8000 units per 4 hours and the imidazole compound in the range of 1 μg–100 μg/kg/minute for a day. When it is to be used with coumarin, drugs these drugs are administered orally at doses of 10 to 15 mg/kg/day and the imidazole compound administered by infusion at a rate of 1 μg–100 μg/kg/minute for a day.

Compositions to be employed in the practice of the present invention whether parenteral, oral or suppository compositions comprises an imidazole compound in a pharmaceutically acceptable carrier.

Parenteral compositions comprise the imidazole compound in sterile physiologically acceptable media such as physiological saline. Such compositioned may also contain other ingredients for purposes such as for aiding solubility or for preservation or the like, said ingredients being those acceptable for intravenous administration. The compositions may be prepared as concentrate compositions and lyophilized and then diluted to the appropriate treating composition immediately prior to administration. A therapeutic composition as a unitary dose form may contain from 100 mg to 10 grams of imidazole compound. Compositions suitable in the preferred practice of the present invention of co-administering plasminogen activator and Factor XIIa inhibitor compound may contain about 58 million I.U. of tissue plasminogen activator (tPA) or 1.5 million I.U. of streptokinase and from 100 mg to 10 grams of the mimdazole compound.

Suppository compositions may be prepared with ointments, jellies, carbowax, polyethylene sorbitan monostearate, polyethyleneglycol, cocoa butter, and other conventional carriers, solid preparations, starches, sugars, diluents, granulating agents, lubricants, binders, disintegrating agents and the like.

The preparation of the imidazole compounds suitable for inhibiting transglutaminase enzymes, particularly Factor XIIIa, and compositions suitable for carrying out the process of the present invention are illustrated by the following examples but are not to be construed as limiting.

EXAMPLE I 2-(7-Peptidyl-2,7-dioxo-heptylthio)-1,3,4,5-tetramethylimidazolium trifluoroacetate
(Peptidyl=GluGlnValSerProLeuThrGlyLeuLys)

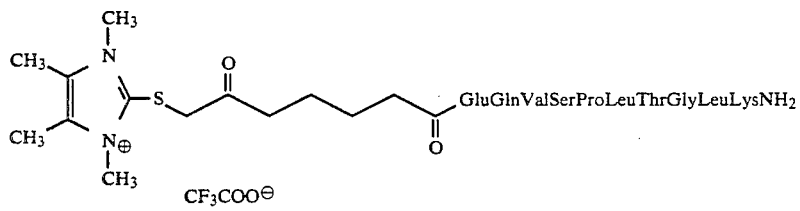

Methyl 6-oxo-7-[1,4,5-trimethylimidazol-2-thio]heptanoate (Compound C)

To a solution of 2.3 grams (0.012 mol) of 1,4,5-trimethyl-2-mercaptoimidazole in 25 milliliters of acetone was added 4.1 milliliters of triethylamine. The reaction mixture was cooled to 0° C. and to it was added dropwise a solution of methyl 7-chloro-6-oxoheptanoate in 20 milliliters of acetone and the resulting mixture stirred overnight at room temperature. At the end of this period the mixture was concentrated to remove the acetone, the residue dissolved in ethyl acetate and the ethyl acetate solution washed successively with water, 5% sodium hydroxide, water and brine, the washed solution dried and then concentrated to obtain 3.2 grams of methyl 6-oxo-7-[3,4,5-trimethylimidazol-2-thio]heptanoate. (Compound C).

6-Oxo-7-[1,4,5-trimethylimidazol-2-thio]heptanoic Acid (Compound D)

To the ester above prepared in 1 milliliter of tetrahydrofuran was added 0.41 milliliter (0.41 millimole) of 1N lithium hydroxide and the resulting mixture stirred for one hour. Then, the solvent was vaporized under reduced pressure, the remaining solution acidified to pH 6.0 and the aqueous solution extracted with ethyl acetate for about two days. Thereafter, the ethyl acetate was vaporized off to obtain 2.09 grams of the 6-oxo-7-(1,4,5-trimethylimidazol-2-thio)heptanoic acid (Compound D, n=4)

D. p-Nitrophenyl 6-oxo-7-[1,4,5-trimethylimidazol-2-thio]heptanoate (Compound E)

833 mg (3.1 mmol) of the acid (D') above prepared, 510 mg of p-nitrophenol and 710 mg of 1-(3-dimethylaminopropyl)-3-ethylcarbodiimide hydrochloride were mixed together in 15.5 milliliters of dry methylene chloride and the mixture stirred overnight at room temperature. The mixture was diluted with ethyl acetate and the ethyl acetate solution washed successively with water, bicarbonate solution, and brine, then dried and concentrated to obtain 1.04 grams of nitrophenyl ester product.

E. 1,3-Dimethyl-2-[7-(4-nitrophenoxy)-2,7-dioxoheptylthio]imidazolium trifluoromethanesulfonate To the nitrophenyl ester above prepared (1.10 grams, 2.6 mmol) in 65 milliliters of dry methylene chloride cooled to about −15° C. was added 0.43 g (2.6 mmol) of methyl trifluoromethanesulfonate and the resulting mixture stirred at room temperature for 2 hours. The solvent was vaporized off to obtain 1.5 grams of the desired 1,3-dimethyl 2-[7-(4-nitro phenoxy)-2,7-dioxoheptylthio]imidazolium trifluoromethanesulfonate.

F. 2-(7-Peptidyl-2,7-dioxo-heptylthio)-1,3,4,5-tetramethylimidazolium trifluoroacetate 200 mg (0.36 mmol) of the ester above prepared, 55 mg (0.36 mmol) of hydroxybenzotriazole and 500 mg (0.12 mmol) of a previously prepared 10-member polypeptide (hereinafter described) were mixed together in 2 milliliters of dimethylformamide and the mixture shaken at room temperature for about 3½ hours, then overnight. Thereafter, the resin was washed with DMF, new reagent added, and stirred overnight to obtain 0.46 gram of the resin bearing the imidazolium peptide (Compound G).

The resin was removed from the peptide with 4.6 milliliters of trifluoroacetic acid and trifluoromethanesulfonic acid (about 0.46 mL) to obtain a precipitate which was filtered and dried at high vacuum. The residue was purified by liquid chromatography to obtain the peptidyl imidazolium trifluoroacetate.

FAB Mass Spectral Data: M+ 1351.4.

EXAMPLE II 2-(7-Peptidyl-2,7-dioxoheptylthio)-1,4,5-trimethylimidazole

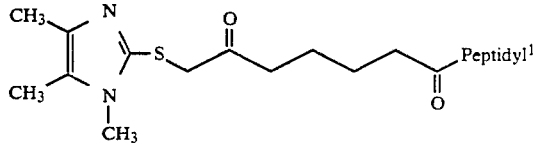

[1]Peptidyl = Glu—Gln—Val—Ser—Pro—Leu—Thr—Gly—Leu—Lys

This example illustrates preparation from the imidazole acid.

102 milligrams (0.36 mmol) of 6-oxo-7-[1,4,5-trimethylimidazol-2-yl]-thioheptanoic acid, 55 milligrams (0.36 mmol) of hydroxybenzotriazole, and 0.36 milliliter (0.36 mmol) of 1M (in methylene chloride) dicyclohexylcarbodiimide and 500 milligrams (0.12 mmol) of the 10 amino acid peptide resin (of Example I) were combined in 2 milliliters of dimethylformamide and shaken overnight at room temperature. At the end of this time the peptide resin was washed and dried under high vacuum and then intimately contacted with hydrofluoric acid (about 25 ml) to remove the resin and to obtain 2-(7-peptidyl-2,7-dioxoheptylthio)-1,4,5-trimethylimidazole product.

EXAMPLE III

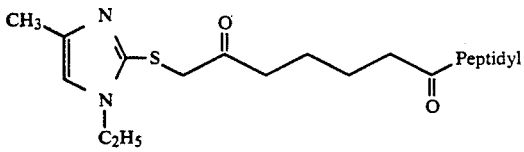

In a similar operation, 102 milligrams (0.36 mmol) of 6-oxo-7-[1-ethyl-4-methyl-imidazol-2-yl]-thio-heptanoic aicd, 55 milligrams (0.36 mmol) of hydroxybenzotriazole, and 0.36 milliliter (0.36 mmol) of 1M dicyclohexyl carbodiimide in methylene chloride and 500 milligrams (0.12 mmol) of the 10 amino peptide resin (of Examples I and II) are combined in 2 milliliters of dimethylformamide and shaken overnight at room temperature. At the end of this period the peptide resin is washed and dried and then contacted with hydrofluoric acid to remove the resin and to obtain 1-ethyl-2-(7-peptidyl-2,7-dioxoheptylthio)-4-methylimidazole product.

EXAMPLE IV

Parenteral Composition

One liter of a parenteral composition comprising one of the foregoing compounds may be prepared from the following formulation:

|  | Grams |
| --- | --- |
| Imidazolium salt | 5.0 |
| Polysorbate 80 | 2.0 |
| Sodium Chloride | 9.0 |
| Sodium carboxymethyl cellulose | 10.0 |
| Methyl paraben | 1.8 |
| Propyl paraben | 0.2 |
| Water, USP q.s. to | 1 liter |

The parabens, sodium chloride and carboxymethylcellulose are dissolved in one-half the total volume of water by heating to 95° C. to obtain a solution which is then filtered and autoclaved. The polysorbate is dissolved in one-third of the total volume of water, and the resulting solution also filtered and autoclaved. Sterile active ingredient is added to the second solution and the mixture passed through a sterile colloid mill to obtain a dispersion of active ingredient. The first solution is added to the suspension with stirring then U.S.P. water added to 1 liter. Sterile vials are filled with the liquid composition while stirring.

PREPARATION OF STARTING MATERIALS

Representative Preparation of a Peptide Glu-Gln-Val-Ser-Pro-Leu-Thr-Gly-Leu-Lys-NH$_2$ 15 grams (9.75 mmol) of methylbenzhydrylamine resin was washed successively with three 150 milliliters portions of 10 percent diisopropylamine, 150 milliliters of methylene chloride and finally 150 milliliters of dimethylformamide, and the solvent then removed by filtration.

To the resin was added for the first coupling, 40 milliliters of dimethylformamide containing 16.2 grams (0.039 mol) of α-BOC-ε-2-Cl-CBZ-L-lysine (lysine protected at the α-amino with t-butoxycarboxyl and at the ε-amino with 2-chlorocarbobenzyloxy); 6.0 grams (0.039 mol) of HOBT.H$_2$O (hydroxybenzotriazole hydrate) and 39 milliliters of 1 molar DCC (dicyclohexylcarbodiimide) in methylene chloride. The resulting mixture was stirred until the Kaiser test indicated completion of the coupling. Thereafter, the coupled product was washed successively several times with dimethylformamide, then with 3:1 methylene chloride/methanol and finally with methylene chloride. The protecting BOC group then was removed by washing the coupled resin three times with 33 percent trifluoroacetic acid in methylene chloride, then several times with each of methylene chloride, 10 percent diisopropylethylamine in dimethylformamide, ethylene chloride and finally dimethylformamide.

To the lysine coupled resin, then was added, 9.7 grams (0.039 mol) of protected leucine (BOC-L-leucine hydrate), 6.0 grams (0.039 mol) HOBT.H$_2$O and 39 milliliters of 1 molar DCC in methylene chloride and the mixture stirred until the Kaiser test showed completion of the coupling. Then, the washing procedure and the de-protection procedure used in lysine was repeated.

Following this, the sequence was repeated employing for the amino acid addition step, the following: 6.8 gram (0.039 mol) t-BOC-L-glycine; 12.1 gram (0.039 mol) N-α-t-BOC, O-benzyl-L-threonine, 9.7 gram (0.039 mol) t-BOC-L-leucine hydrate; 8.4 gram (0.039 mol) t-BOC-L-proline; 11.5 grams (0.039 mol) t-BOC-O-benzyl-L-serine; 8.5 grams 90.039 mol) t-BOC-L-valine. At this point, the 7 component polypeptide was checked for relative amounts of amino acid in the Spinco test (Stanford Moore et. al., "Chromatographic Determination of Amino Acids by the Use of Automatic Recording Equipment" in *Methods of Enzymology*, Vol. 6, pp. 819-822 (1963)). Then 9.6 grams (0.039 mol) N-α-tBOC-L-glutamine as activated (with HOBT and DCC) was coupled; finally, 13.2 grams (0.039 mol) of t-BOC-L-glutamic acid α benzyl ester was coupled in situ. After the completion of the coupling and the removal of the t-BOC, and completion of the washings, the solvents were completely drained from the resin and the latter dried in a vacuum overnight to obtain 19.1 grams of peptide bearing resin.

The peptide bearing resin was used in the preparations as peptide/resin. After coupling with the desired imidazole compound the resin was cleaved from the peptide by intimately contacting either with a combination of trifluoroacetic acid and methyl trifluoromethanesulfonate (TFA/TFMSA) or hydrofluoric acid.

When the cleaving agent was TFA/TFMSA, about 1/100 part by weight of TFA and 1/1000 part by weight of TFMSA were employed. Thus, for 500 milligrams of peptide about 5 milliliters of TFA and 500 microliters of TFMSA should be satisfactory.

When the cleaving reagent is hydrofluoric acid, about 1/20 part by weight of HF is employed. Thus, for 500 milligrams of peptide about 25 (20 to 30 ml) milliliters of HF may be employed.

GENERAL PREPARATION OF 2-MERCAPTOIMIDAZOLE

The 2-mercaptoimidazoles may be obtained by a reaction between an appropriate acyloin and mono-substituted thiourea according to the following equation:

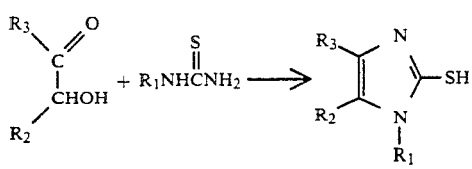
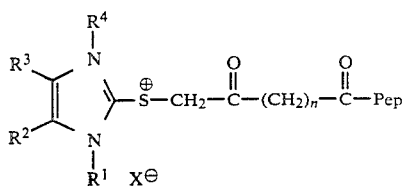

The reaction may be carried out by fusing the reactants or by refluxing the components in hexanol-1 as more fully described by Nuhn, P. et al., J. fur praktische Chemie, 312, 90 (1970) for the fusion method and by Kjellin, G. et. al., Acta Chemica Scandinavica, 23, 2879 (1969) for the method where the α-hydroxyketones and N-alkylthioureas are refluxed in 1-hexanol with a water separator. The teachings of the starting 2-mercaptoimidazoles are incorporated by reference.

The acyloins may be prepared in any manner within the knowledge of those skilled in the art.

What is claimed is:

1. A composition suitable for thrombolytic therapy in unit dosage form comprising (1) about 58 million I.U. of tissue plasminogen activator (tPA) or about 1.5 million I.U. of streptokinase as plasminogen activator and (2) from 100 mg to 10 grams of an imidazole compound selected from the group consisting of:

(A) an imidazole having the formula

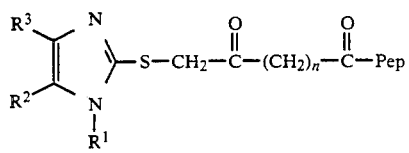

(B) an imidazolium salt having the formula wherein in the above formulas $R_1$ is lower alkyl $R_2$ and $R_3$ are independently hydrogen or lower alkyl $R_4$ is lower alkyl Pep is a peptidyl chain of 2 to 10 amino acids which is attached to the carbonyl through the Ω amino group of the first amino acid and which terminates with the carboxyl group of the last amino acid in an amide linkage.; and X is a negative radical of a pharmaceutically acceptable salt; and n is from 2 to 5 admixture with a pharmaceutically acceptable carrier.

2. A composition according to claim 1 wherein the plasminogen activator is streptokinase.

3. A method for inhibiting hard clot formation or supplementing fibrinolytic therapy comprising administering to a patient in need of such treatment an imidazole compound of claim 1 in an amount effective for inhibiting hard clot formation or supplementing fibrinolytic therapy.

4. A method according to claim 3 wherein the imidazole compound is administered to provide about 1 μg to 100 μg/kg/minute for a day (1440 minutes).

5. A method according to claim 3 wherein an antithrombotic agent is also administered.

6. A method according to claim 5 wherein the antithrombotic agent is platelet aggregation inhibitor.

7. A method according to claim 5 wherein the antithrombotic agent is an anticoagulant.

* * * * *